United States Patent
Meadows et al.

(10) Patent No.: US 8,676,345 B2
(45) Date of Patent: *Mar. 18, 2014

(54) ELECTRODES FOR STIMULATION LEADS AND METHODS OF MANUFACTURE AND USE

(71) Applicant: Boston Scientific Neuromodulation Corporation, Valencia, CA (US)

(72) Inventors: Paul M. Meadows, Glendale, CA (US); Randall Lee Brase, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/063,676

(22) Filed: Oct. 25, 2013

(65) Prior Publication Data

US 2014/0052229 A1    Feb. 20, 2014

Related U.S. Application Data

(63) Continuation of application No. 12/427,935, filed on Apr. 22, 2009, now Pat. No. 8,600,518.

(60) Provisional application No. 61/049,237, filed on Apr. 30, 2008.

(51) Int. Cl.
*A61N 1/00* (2006.01)

(52) U.S. Cl.
USPC ............ 607/116; 607/117; 607/119; 607/122

(58) Field of Classification Search
USPC ..................... 607/116, 117, 119, 122; 29/854
See application file for complete search history.

(56) References Cited

U.S. PATENT DOCUMENTS

| | | | |
|---|---|---|---|
| 3,738,368 A | 6/1973 | Avery et al. |
| 3,774,618 A | 11/1973 | Avery |
| 4,112,941 A | 9/1978 | Larimore |
| 4,135,518 A | 1/1979 | Dutcher |

(Continued)

FOREIGN PATENT DOCUMENTS

WO    2008035285 A2    3/2008

OTHER PUBLICATIONS

U.S. Appl. No. 12/427,935 Official Communication mailed May 3, 2011.

(Continued)

*Primary Examiner* — Niketa Patel
*Assistant Examiner* — William Levicky
(74) *Attorney, Agent, or Firm* — Frommer Lawrence & Haug LLP; Bruce E. Black

(57) ABSTRACT

An electrode has a unitary ring with an exterior surface, interior surface, and at least two edges. The electrode also includes a seat formed in at least the exterior surface of the unitary ring. The seat is configured and arranged for attachment of a terminal end of a lead wire, disposed in the seat, to the electrode. A lead includes a lead body; a plurality of electrodes disposed at the distal end of the lead body; and a plurality of lead wires. Each electrode includes a unitary ring and a seat in the unitary ring. The unitary ring has an exterior surface and an interior surface and defines a hollow center region. The seat is formed as a depression of a portion of the unitary ring. Each of the lead wires extends along the lead body and is attached to a corresponding electrode at the seat of the corresponding electrode.

20 Claims, 8 Drawing Sheets

(56) References Cited

U.S. PATENT DOCUMENTS

| | | |
|---|---|---|
| 4,273,135 A | 6/1981 | Larimore et al. |
| 4,607,644 A | 8/1986 | Pohndorf |
| 4,633,880 A | 1/1987 | Osypka et al. |
| 4,711,027 A | 12/1987 | Harris |
| 4,735,208 A | 4/1988 | Wyler et al. |
| 4,835,853 A | 6/1989 | Hirschberg |
| 4,979,511 A | 12/1990 | Terry, Jr. |
| 5,000,194 A | 3/1991 | van den Honert et al. |
| 5,014,720 A | 5/1991 | Barcel et al. |
| 5,037,497 A | 8/1991 | Stypulkowski |
| 5,251,634 A | 10/1993 | Weinberg |
| 5,344,438 A | 9/1994 | Testerman et al. |
| 5,366,493 A | 11/1994 | Scheiner et al. |
| 5,458,629 A | 10/1995 | Baudino et al. |
| 5,505,201 A | 4/1996 | Grill, Jr. et al. |
| 5,531,778 A | 7/1996 | Maschino et al. |
| 5,683,431 A | 11/1997 | Wang |
| 5,728,149 A | 3/1998 | Laske et al. |
| 5,843,147 A | 12/1998 | Testerman et al. |
| 5,935,465 A | 8/1999 | Cardineau et al. |
| 5,964,793 A | 10/1999 | Rutten et al. |
| 6,055,456 A | 4/2000 | Gerber |
| 6,091,979 A | 7/2000 | Madsen |
| 6,181,969 B1 | 1/2001 | Gord |
| 6,185,463 B1 | 2/2001 | Baudino |
| 6,208,882 B1 | 3/2001 | Lenarz et al. |
| 6,216,045 B1 | 4/2001 | Black et al. |
| 6,236,892 B1 | 5/2001 | Feler |
| 6,289,250 B1 | 9/2001 | Tsuboi et al. |
| 6,330,481 B1 | 12/2001 | Van Wijk et al. |
| 6,421,567 B1 | 7/2002 | Witte |
| 6,456,888 B1 | 9/2002 | Skinner et al. |
| 6,501,993 B2 | 12/2002 | Morgan et al. |
| 6,505,401 B1 | 1/2003 | Doan |
| 6,516,227 B1 | 2/2003 | Meadows et al. |
| 6,587,733 B1 | 7/2003 | Cross, Jr. et al. |
| 6,597,953 B2 | 7/2003 | Boling |
| 6,600,956 B2 | 7/2003 | Maschino et al. |
| 6,606,521 B2 | 8/2003 | Paspa et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,757,970 B1 | 7/2004 | Kuzma et al. |
| 7,047,081 B2 | 5/2006 | Kuzma |
| 7,107,097 B2 | 9/2006 | Stern et al. |
| 7,127,295 B2 | 10/2006 | Evans |
| 7,162,310 B2 | 1/2007 | Doan |
| 7,221,981 B2 | 5/2007 | Gliner |
| 7,231,259 B2 | 6/2007 | Jenney et al. |
| 7,437,193 B2 | 10/2008 | Parramon et al. |
| 7,467,016 B2 | 12/2008 | Colborn |
| 7,787,961 B1 | 8/2010 | Safarevich et al. |
| 2003/0144719 A1 | 7/2003 | Zeijlemaker |
| 2004/0024440 A1 | 2/2004 | Cole |
| 2004/0059392 A1 | 3/2004 | Parramon et al. |
| 2004/0068313 A1 | 4/2004 | Jenney et al. |
| 2005/0021119 A1 | 1/2005 | Sage et al. |
| 2005/0113896 A1 | 5/2005 | Pavlik et al. |
| 2005/0177039 A1 | 8/2005 | Mills et al. |
| 2007/0027512 A1 | 2/2007 | Chan et al. |
| 2007/0027513 A1 | 2/2007 | Chan et al. |
| 2007/0168004 A1 | 7/2007 | Walter |
| 2007/0168007 A1 | 7/2007 | Kuzma et al. |
| 2007/0203537 A1 | 8/2007 | Goetz et al. |
| 2008/0027524 A1 | 1/2008 | Maschino et al. |
| 2008/0172116 A1 | 7/2008 | Mrva et al. |
| 2008/0183224 A1 | 7/2008 | Barolat |
| 2008/0183258 A1 | 7/2008 | Inman |
| 2009/0030493 A1 | 1/2009 | Colborn et al. |
| 2009/0099439 A1 | 4/2009 | Barolat |
| 2009/0276021 A1 | 11/2009 | Meadows et al. |

OTHER PUBLICATIONS

U.S. Appl. No. 12/427,935 Official Communication mailed Sep. 1, 2011.
U.S. Appl. No. 12/427,935 Official Communication mailed Feb. 13, 2012.
U.S. Appl. No. 12/427,935 Official Communication mailed Apr. 5, 2012.
U.S. Appl. No. 12/427,935 Appeal Brief filed Jun. 28, 2012.
U.S. Appl. No. 12/427,935 Official Communication mailed Aug. 9, 2012.
U.S. Appl. No. 12/427,935 Appeal Brief filed Dec. 27, 2012.
U.S. Appl. No. 12/427,935 Official Communication mailed Feb. 26, 2013.
U.S. Appl. No. 12/427,935 Official Communication mailed Apr. 19, 2013.
U.S. Appl. No. 12/427,935 Official Communication mailed Jul. 15, 2013.

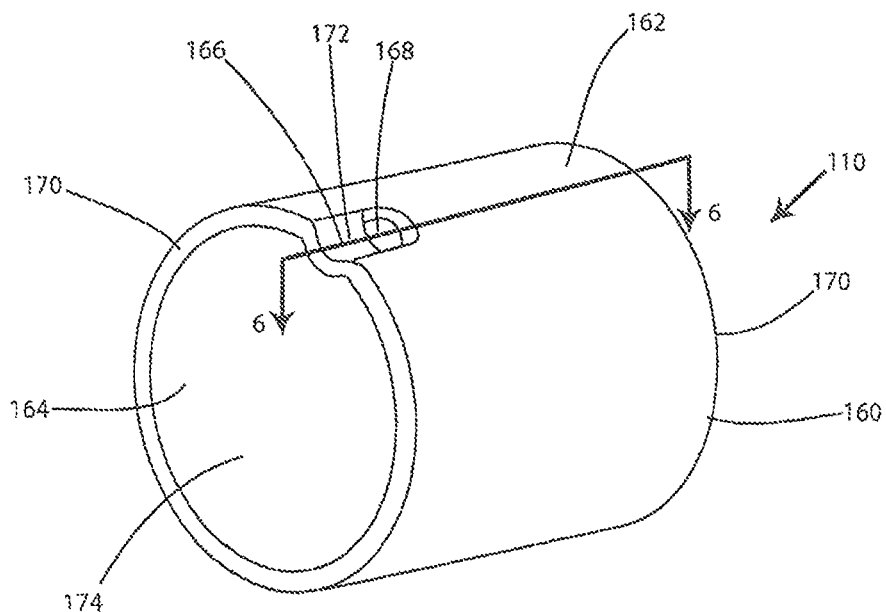
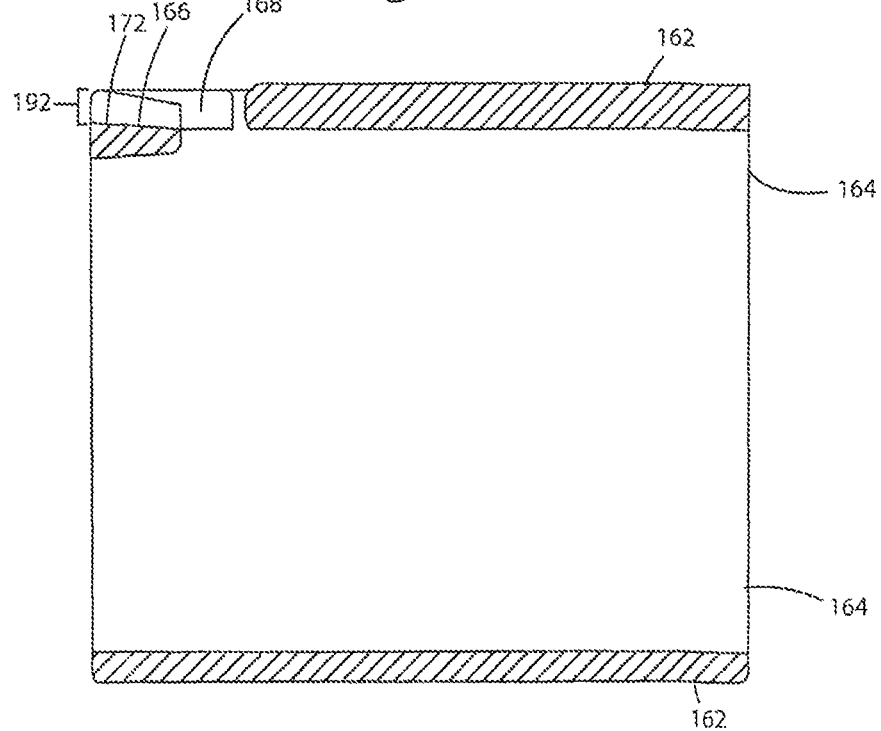

ELECTRODES FOR STIMULATION LEADS AND METHODS OF MANUFACTURE AND USE

CROSS REFERENCE TO RELATED APPLICATIONS

This application is a continuation of U.S. patent application Ser. No. 12/427,935, filed Apr. 22, 2009, now allowed, which claims the benefit of U.S. Provisional Patent Application Ser. No. 61/049,237, filed Apr. 30, 2008, all of which are incorporated herein by reference.

FIELD OF THE INVENTION

The invention is directed to electrodes and methods of making and using the electrodes. The invention is also directed to electrodes with a seat for receiving a conductor, as well as stimulation devices containing the electrodes and methods of manufacturing and using the electrodes and stimulation devices.

BACKGROUND OF THE INVENTION

Stimulation devices have been developed to provide therapy for a variety of disorders, as well as for other treatments. For example, stimulation devices can be used to stimulate nerves (such as the spinal cord), muscles, or other tissue. A stimulation device typically includes a control module (with a pulse generator), one or more leads, and an array of stimulator electrodes on each lead. The stimulator electrodes can be implanted in contact with or near the nerves, muscles, or other tissue to be stimulated. The pulse generator in the control module generates electrical pulses that are delivered by the electrodes to body tissue. As an example, electrical pulses can be provided to the dorsal column fibers within the spinal cord to provide spinal cord stimulation.

The stimulator electrodes are coupled to the control module by the lead and the control module is typically implanted elsewhere in the body, for example, in a subcutaneous pocket. The lead is often anchored at one or more places in the body to prevent or reduce movement of the lead or stimulator electrodes within the body which could damage tissue, move the stimulator electrodes out of the desired position, or interrupt the connection between the stimulator electrodes and the control module.

BRIEF SUMMARY OF THE INVENTION

One embodiment is an electrode having a unitary ring with an exterior surface, an interior surface, and at least two edges. The electrode also includes a seat formed in at least the exterior surface of the unitary ring. The seat is configured and arranged for attachment of a terminal end of a lead wire, disposed in the seat, to the electrode.

Another embodiment is a lead including a lead body; a plurality of electrodes disposed at the distal end of the lead body; and a plurality of lead wires. Each electrode includes a unitary ring and a seat in the unitary ring. The unitary ring has an exterior surface and an interior surface and defines a hollow center region. The seat is formed as a depression of a portion of the unitary ring. Each of the lead wires extends along the lead body and is attached to a corresponding electrode at the seat of the corresponding electrode.

Yet another embodiment is a method of making a system for stimulation. The method includes providing an electrode having a unitary ring with an exterior surface, an interior surface, and a seat formed by depressing a portion of the unitary ring. A lead wire is disposed within the seat of the electrode and a terminal end of the lead wire is coupled to the seat of the electrode.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 5 is a schematic perspective view of one embodiment of an electrode, according to the invention;

FIG. 6 is a schematic cross-sectional view of one embodiment of the electrode of FIG. 5 at line 6-6, according to the invention;

DETAILED DESCRIPTION OF THE INVENTION

The invention is directed to electrodes and methods of making and using the electrodes. The invention is also directed to electrodes with a seat for receiving a conductor, as well as stimulation devices containing the electrodes and methods of manufacturing and using the electrodes and stimulation devices.

Figure 1:
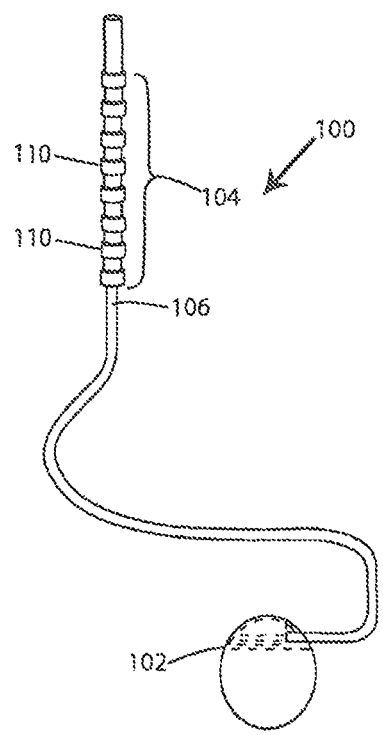
FIG. 1 is a schematic view of one embodiment of a stimulator system, according to the invention.

FIG. 1 illustrates schematically an implantable stimulation device 100, such as a spinal cord stimulator. The implantable stimulation device includes a control module 102, an electrode array 104, and a lead 106 coupling the control module to the electrode array. It will be understood that the system for stimulation can include more, fewer, or different components and can have a variety of different configurations including those configurations disclosed in the stimulator references cited herein. The control module 102 typically includes a pulse generator that provides pulses of stimulation current to electrodes of the electrode array 104. The control module 102 may also include a power source for generating the stimulation current or may receive power from an external source. The power source can be any available power source including batteries, such as primary batteries or rechargeable batteries. Examples of other power sources include, but are not limited to, super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

The control module 102 is optionally programmable to allow programming of one or more functions such as, for example, the selection of electrodes for stimulation, the selection of electrodes as anode or cathode, the amplitude of the stimulation current, the duration of the stimulation current, and the periodicity of the stimulation current. In some embodiments, the control module 102 can be accessed using a programming unit external to the body of the patient to alter or modify these functions.

The electrode array 104 typically includes one or more electrodes 110. In some embodiments, the electrode array 104 includes three, four, five, six, seven, eight, nine, ten or more electrodes 110. The electrodes are disposed around the circumference of a lead, such as in a percutaneous lead.

The lead 106 includes a set of lead wires (for example, one lead wire per electrode of the electrode array) within a non-conductive sheathing. Each lead wire couples one or more electrodes to a terminal on the proximal end of the lead. The proximal end is inserted into the control module where the terminals are coupled to contacts of the control module. Non-limiting examples of suitable control modules and leads are illustrated in U.S. Pat. Nos. 6,181,969; 6,516,227; 6,609,029; 6,609,032; and 6,741,892, all of which are incorporated herein by reference.

The electrodes of the invention may be used with other common stimulation devices including cardiac pacing leads, which typically may have one or two electrodes on the lead. Still other stimulation devices include various implantable defribrillators.

Figure 2:
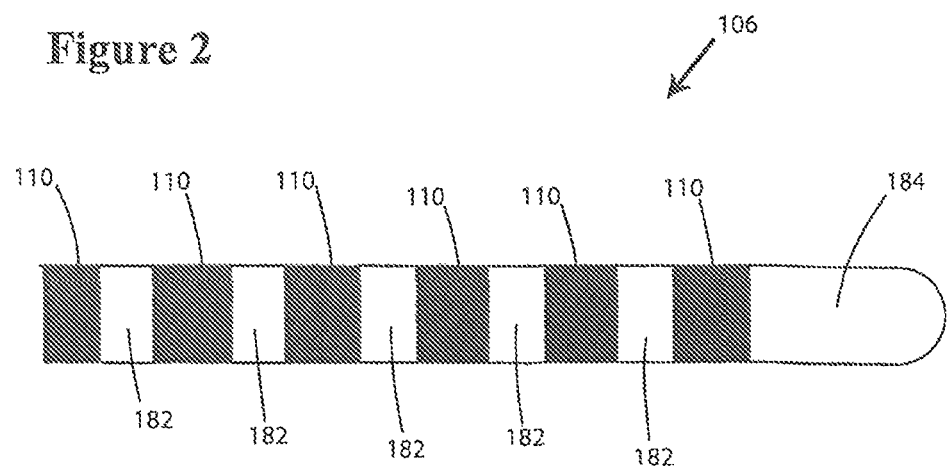
FIG. 2 is a schematic side view of one embodiment of a lead, according to the invention.

FIG. 2 is a schematic representation of one embodiment of a lead 106. The lead 106 includes one or more electrodes 110. Preferably, the electrodes 110 are separated from one another and are disposed in a spaced apart arrangement as illustrated schematically in FIG. 2. The distance between adjacent electrodes 110 may be relatively constant across the electrode array as illustrated in FIG. 2. Alternatively, the distances between adjacent electrodes 110 may vary.

Figure 11A:
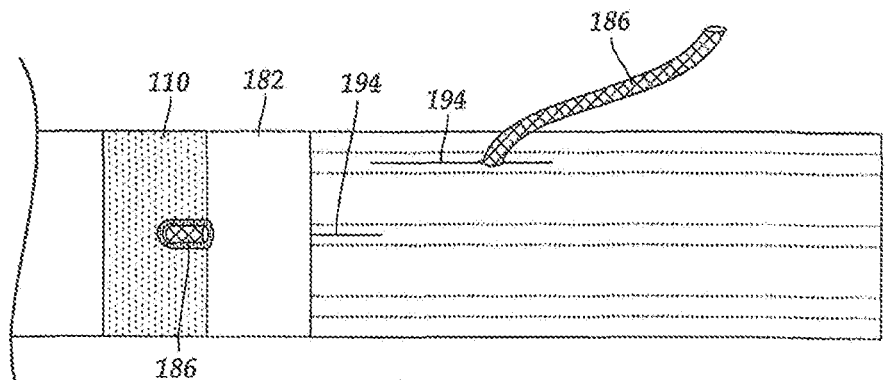
FIGS. 11A-C illustrate steps in a first method for partially assembling a lead, according to the invention.
Figure 11B:
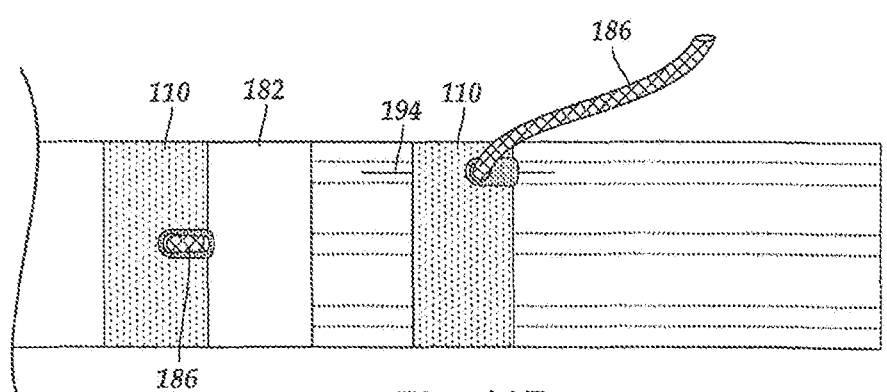
Figure 11C:
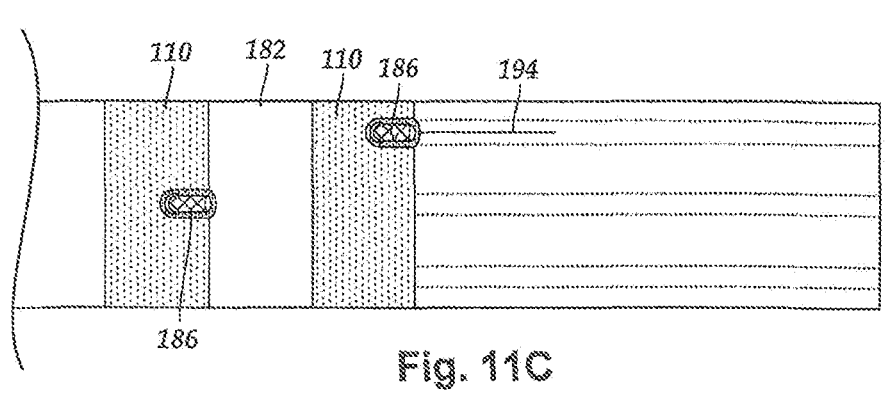

The lead optionally includes spacers 182. Preferably, the spacers 182 are disposed between the electrodes 110 as illustrated in FIG. 2. The spacers 182 preferably have a hollow center area such that the spacers 182 can be threaded onto a lumen tube 176 (see FIGS. 3 and 11) or can be used as a part of the lead body to separate the electrodes. The lead 106 may also include an end spacer 184. The end spacer 184 is disposed at the distal end of the lead 106. The end spacer 184 may have any shape, but is preferably rounded at the distal end as illustrated schematically in FIG. 2. The spacers 182 and the end spacer 184 can be made of any non-conductive biocompatible material including, for example, silicone, polyurethane, and polyetheretherketone (PEEK). The spacers 182, 184 help electrically isolate the electrodes 110. Additionally or alternatively, the electrodes can be disposed over portions of a contiguous, non-conducting lead body with an opening through the lead body to allow the conductor to be coupled to the electrode.

The outer diameter of the electrode 110 may be the same as the outer diameter of the spacers 182, 184 of the lead 106 as illustrated in FIG. 2. The outer diameter of the electrode 110 may alternatively be greater than the outer diameter of the spacers 182, 184 such that the electrode 110 is raised above the spacers 182, 184 as illustrated schematically in FIG. 1. Alternatively, the outer diameter of the spacers 182, 184 may be greater than the outer diameter of the electrodes 110 such that the electrodes are recessed.

Figure 3:
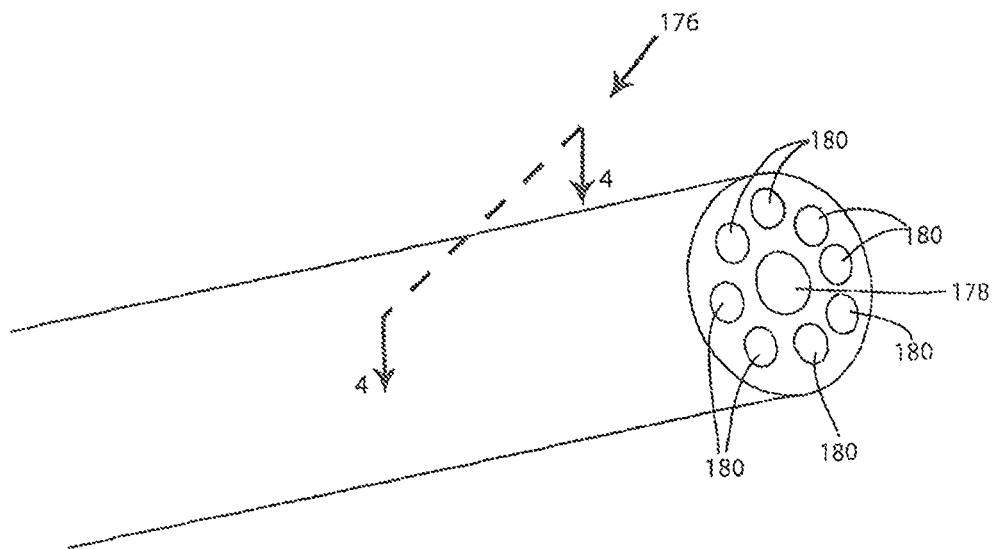
FIG. 3 is a schematic perspective view of one embodiment of a lumen tube, according to the invention.

The lead 106 can include one or more lumens disposed through at least a portion of the length of the lead, as illustrated schematically in FIG. 3. The lumens can be formed in a lumen tube 176. A cross-sectional view of the lumen tube 176 of FIG. 3 at line 4-4 is illustrated schematically in FIG. 4. The lumen tube 176 may be made of any non-conductive biocompatible material including, for example, silicone, polyurethane, and polyetheretherketone (PEEK). In some embodiments, the lead 106 includes one or more peripheral lumens 180 (see FIGS. 3 and 4). In at least some embodiments, the number of peripheral lumens 180 is equal to the number of electrodes 110.

Figure 4:
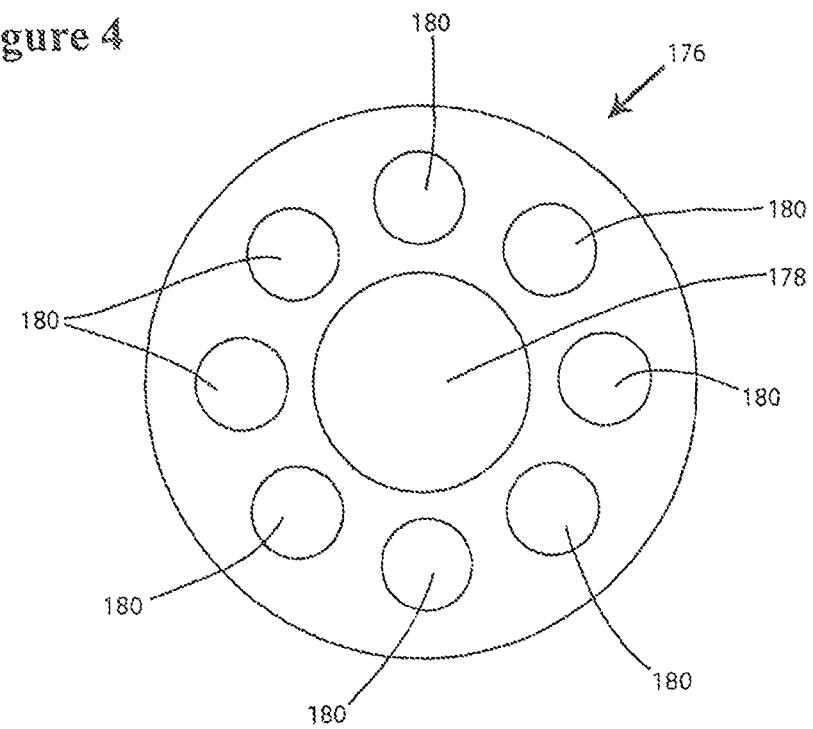
FIG. 4 is a schematic cross-sectional view of the lumen tube of FIG. 3 at line 4-4, according to the invention.

The lead 106 may also include a central lumen 178 as illustrated in FIGS. 3 and 4. The central lumen 178 can be configured and arranged to receive a stylet. In the illustrated embodiment, the peripheral lumens 180 are configured and arranged to receive at least one lead wire 186. The peripheral lumens 180 are preferably disposed around the circumference of the lead 106 and are preferably disposed around the central lumen 178, if any, as illustrated schematically in FIGS. 3 and 4. As will be recognized by those of skill in the art, other arrangements of lumens within the lumen tube are also possible.

FIG. 5 is a schematic representation of one embodiment of an electrode 110. The electrode 110 includes a unitary ring 160. The unitary ring 160 may be made of any conductive bio-compatible material including, for example, metals, metal alloys (e.g., 80% platinum/20% iridium alloy, MP35N, MP LT, etc.), conductive polymers, and conductive carbon. The unitary ring 160 has an exterior surface 162, an interior surface 164, and at least two edges 170 disposed between the exterior surface 162 and the interior surface 164. The unitary ring 160 defines a hollow center region 174.

Preferably, the unitary ring 160 is a continuous ring and preferably does not have any seams such as weld joints. Such electrodes 110 comprising a unitary ring 160 therefore are not susceptible to failures of weld joints, etc. that hold the electrode together.

The electrode 110 includes a seat 166. The seat 166 is a depression in at least the exterior surface 162 of the unitary ring 160. The seat 166 may deform both the exterior surface 162 and the interior surface 164 of the unitary ring 160 as illustrated schematically in FIG. 5. The seat 166 may be formed by any process including, for example, stamping. The seat 166 is configured and arranged to accept a lead wire 186 (see FIG. 11). Preferably, the seat 166 accepts the terminal end of the lead wire 186. The lead wire 186 optionally passed through a lumen (e.g., lumen 180 of FIG. 3) of the lead body and may pass through an opening in the lead body or a lumen tube to make contact with the electrode.

Figure 9:
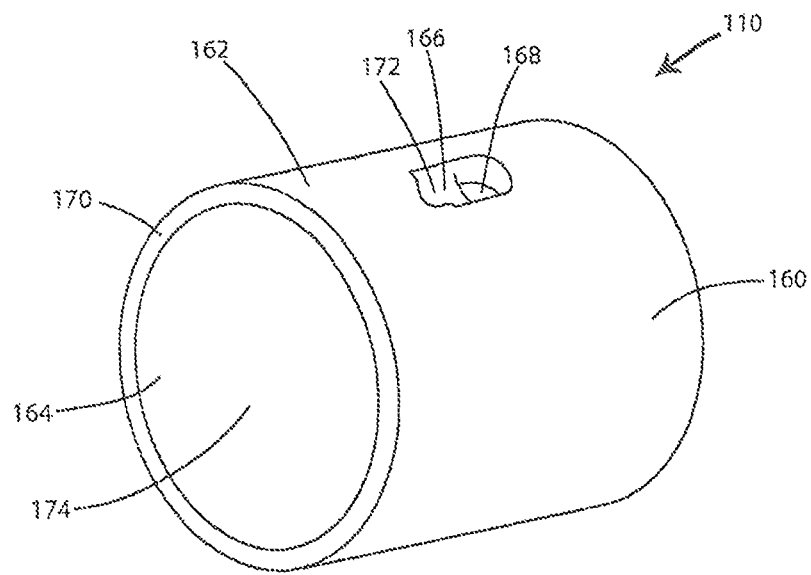
FIG. 9 is a schematic perspective view of a third embodiment of an electrode, according to the invention.

In some embodiments, the electrode 110 includes an opening 168 (see FIGS. 5 and 9). The opening 168 extends from the interior surface 164 of the unitary ring to the exterior surface 162 of the unitary ring, intersects the seat 166, and is spaced apart from the edges 170 of the unitary ring as illustrated schematically in FIG. 5. Preferably, the opening 168 is configured and arranged to accept a lead wire 186.

Figure 10:
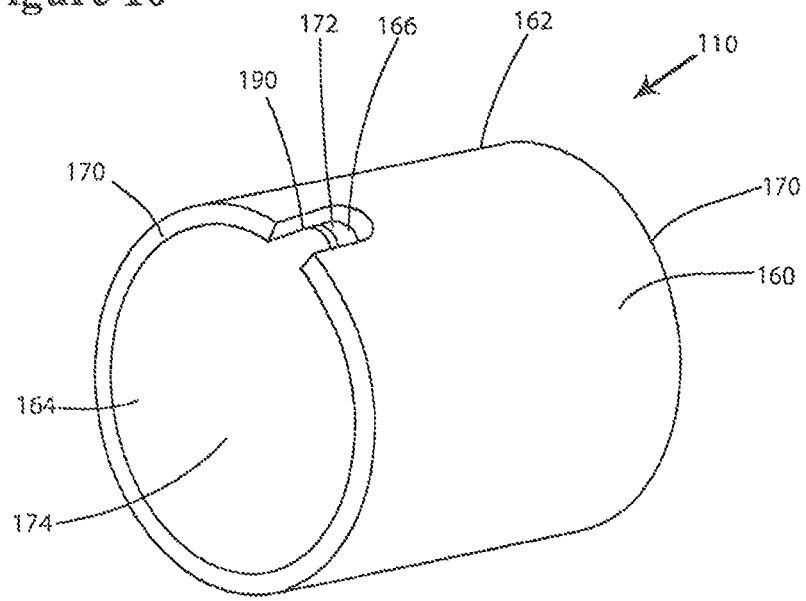
FIG. 10 is a schematic perspective view of a fourth embodiment of an electrode, according to the invention.

Additionally or alternatively, the electrode 110 can include an indentation 190 (see FIG. 10). The indentation 190 extends from the interior surface 164 of the unitary ring to the exterior surface 162 of the unitary ring, intersects the seat 166, and intersects an edge 170 of the unitary ring as illustrated schematically in FIG. 10. Preferably, the indentation 190 is configured and arranged to accept a lead wire 186. It will be recognized that some electrodes with a seat, as described herein, may not include either an opening or indentation.

Figure 7:
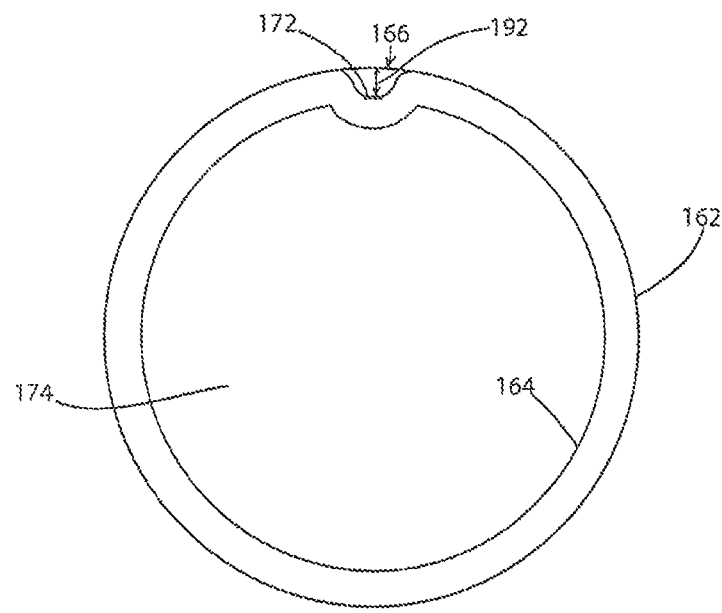
FIG. 7 is a schematic front view of one embodiment of an electrode, according to the invention.

FIG. 6 is a cross-sectional view of the electrode 110 of FIG. 5 along line 6-6. FIG. 7 is a front view of the electrode 110 of FIG. 5. The distance 192 between the lowest point on the exterior surface 172 of the seat and the exterior surface 162 of the unitary ring (see FIGS. 6 and 7) may be less than, equal to, or greater than the diameter of a terminal end of a lead wire, with or without insulation. The distance 192 between the lowest point on the exterior surface 172 of the seat and the exterior surface 162 of the unitary ring is preferably equal to or greater than the diameter of the lead wire with insulation when the electrode 110 does not include an opening 168 or indentation 190. The distance between the lowest point on the exterior surface 172 of the seat and the exterior surface 162 of the unitary ring is preferably equal to the diameter of the lead wire without insulation when the electrode 110 includes an opening 168 or indentation 190.

Figure 8:
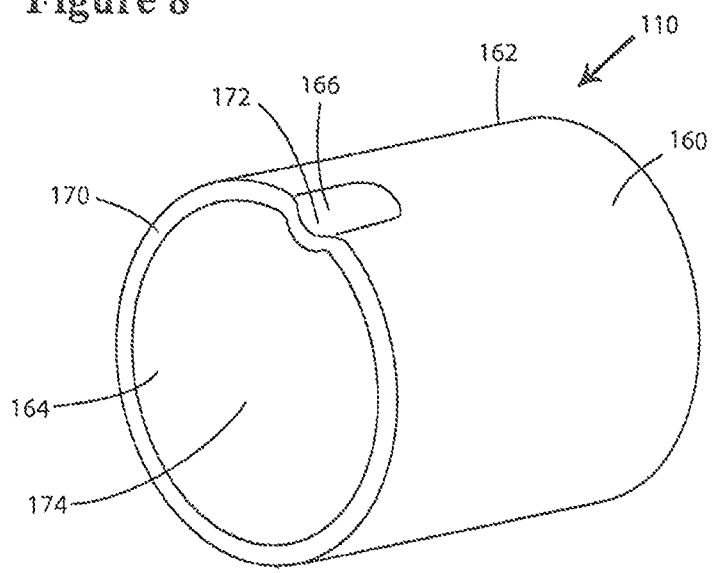
FIG. 8 is a schematic perspective view of another embodiment of an electrode, according to the invention.

FIG. 8 schematically illustrates another embodiment of an electrode 110. This electrode 110 does not have an opening 168 or indentation 190. If the electrode 110 does not include an opening 168 or indentation 190, the seat 166 preferably extends from an edge 170 of the unitary ring 160 as illustrated schematically in FIG. 8.

FIG. 9 schematically illustrates another embodiment of an electrode 110. This electrode 110 has an opening 168 and a seat 166. As illustrated in FIGS. 9 and 5, the opening can be disposed completely within the unitary ring 160 (i.e., not intersect an edge of the unitary ring). The seat 166 can extend away from the opening 168 to an edge 170 of the unitary ring 160 as illustrated schematically in FIG. 5. Alternatively, the seat 166 can extend away from the opening 168, but be disposed completely within the unitary ring 160 (i.e., not intersect an edge of the unitary ring) as illustrated schematically in FIG. 9.

FIG. 10 schematically illustrates yet another embodiment of an electrode 110. This electrode 110 has an indentation 190 that intersects an edge 170 of the unitary ring 160. The seat 166 extends from the indentation 190 away from the edge 170.

The electrode 110 can be made by any method known to those of skill in the art. For example, the conductive material used to make the electrode can be formed as a tubing, which can be cut to the desired length. The electrode can then be placed over a first mandrel and a support mandrel can be inserted into the first mandrel to support a stamping process. A stamping device can be used to form a seat. Additionally, the stamping device can be used to form an opening or indentation in the electrode or a separate device can be used to form the opening or indentation.

A lead 106 may be made by any method known to those of skill in the art. For example, a lumen tube 176 with a lead wire 186 disposed in at least one lumen can be slit to form a passage 194 from the exterior surface of the lumen tube 176 to a lumen 180, as illustrated schematically in FIG. 11A. The lead wire 186 disposed in the slit lumen can then be partially removed from the lumen and threaded through the opening 168 of an electrode 110 as illustrated schematically in FIG. 11A. Next, the electrode 110 is slid over the lumen tube, while holding the lead wire taut. The seat 166 of the electrode 110 can be aligned with the lumen tube such that the seat is disposed over the slit in the lumen tube (see FIG. 11B). The slit in the lumen tube allows the lumen tube material to be deformed as the electrode is pushed into position. The lead wire is then disposed in the seat and attached to the electrode 110 by any method including, for example, welding (see FIG. 11C). A spacer 182 may then be slid onto the lumen tube 176 followed by another electrode 110 as described above.

Figure 12A:
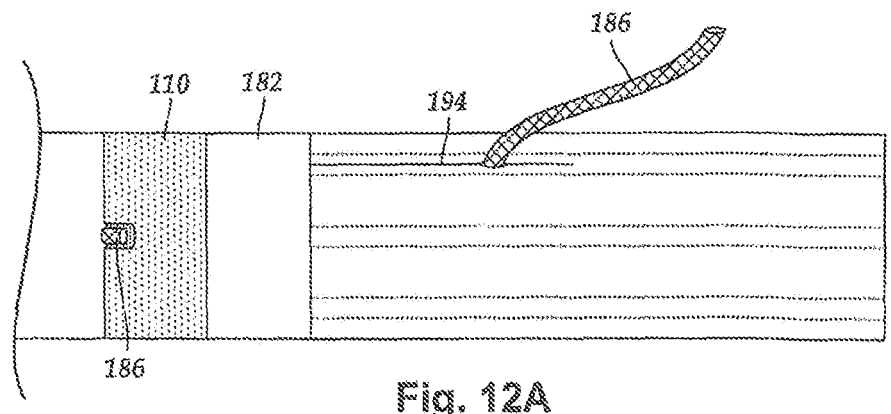
FIG. 12A-C illustrate steps in a second method for partially assembling a lead, according to the invention.
Figure 12B:
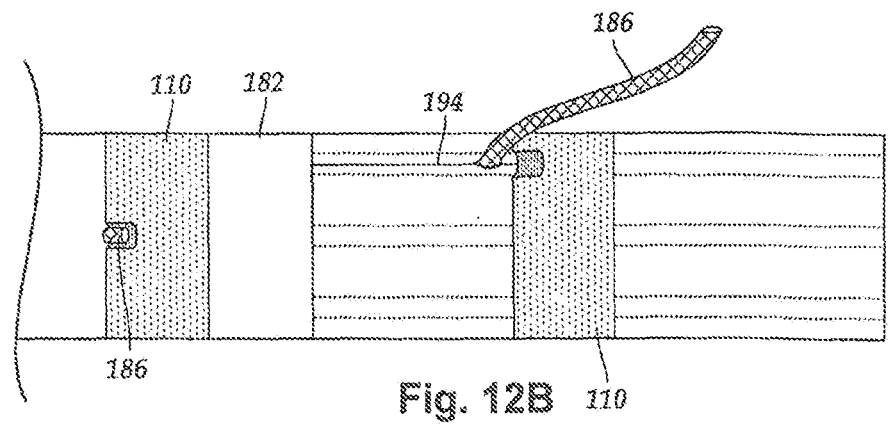
Figure 12C:
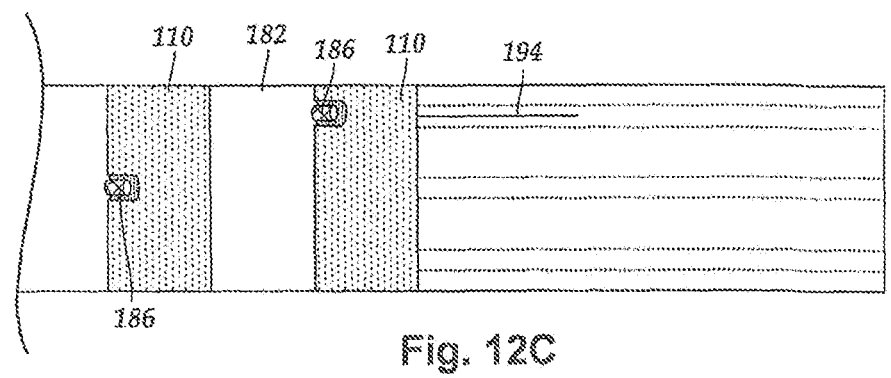

If the electrode 110 does not include an opening 168, instead of threading the lead wire through the opening, the electrode 110 can be slid over the lumen tube and the lead wire, while holding the lead wire taut as illustrated in FIGS. 12A-C. Then the lead wire can be disposed in the seat as illustrated schematically in FIGS. 12A-C.

Figure 13:
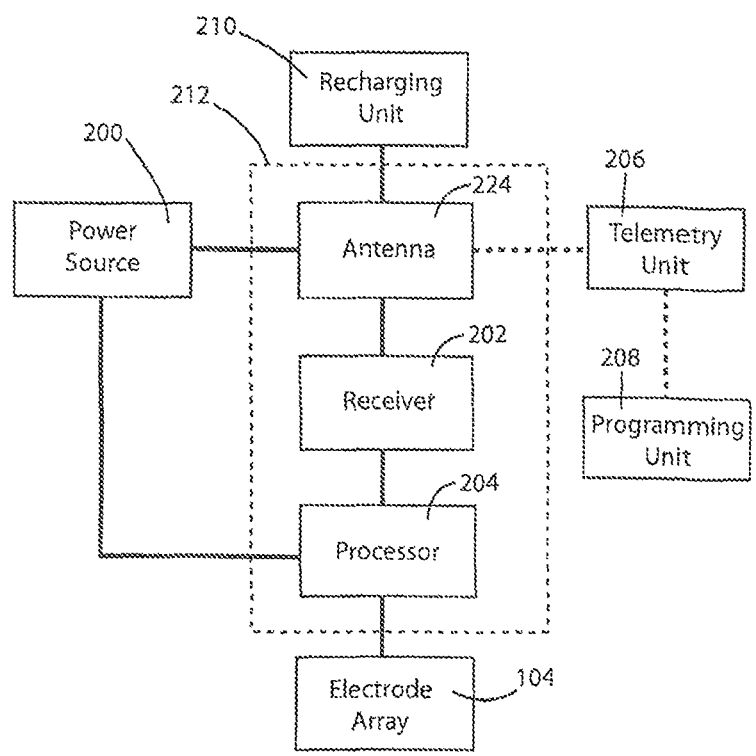
FIG. 13 is a schematic overview of components of one embodiment of a system for stimulation, according to an embodiment of the invention.

FIG. 13 is a schematic overview of one embodiment of components of a system for stimulation, including an electronic subassembly 212 (which may or may not include the power source 200), according to the invention. It will be understood that the system for stimulation and the electronic subassembly 212 can include more, fewer, or different components and can have a variety of different configurations including those configurations disclosed in the stimulator references cited herein. Some or all of the components of the system for stimulation can be positioned on one or more circuit boards or similar carriers within a housing of a stimulator, if desired.

Any power source 200 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 224 or a secondary antenna. The external power source can be in a device that is mounted on the skin of the user or in a unit that is provided near the stimulator user on a permanent or periodic basis.

If the power source 200 is a rechargeable battery, the battery may be recharged using the optional antenna 224, if desired. Power can be provided to the battery for recharging by inductively coupling the battery through the antenna to a recharging unit 210 (see FIG. 13) external to the user. Examples of such arrangements can be found in the stimulator references identified above.

In one embodiment, electrical current is emitted by the electrodes 110 to stimulate motor nerve fibers, muscle fibers, or other body tissues near the stimulator. The electronic subassembly 212 provides the electronics used to operate the stimulator and generate the electrical pulses at the electrodes 110 to produce stimulation of the body tissues. FIG. 13 illustrates one embodiment of components of the electronic subassembly and associated units.

In the illustrated embodiment, a processor 204 is generally included in the electronic subassembly 212 to control the timing and electrical characteristics of the stimulator. For example, the processor can, if desired, control one or more of the timing, frequency, strength, duration, and waveform of the pulses. In addition, the processor 204 can select which electrodes can be used to provide stimulation, if desired. In some embodiments, the processor may select which electrode(s) are cathodes and which electrode(s) are anodes. In some embodiments with electrodes disposed on two or more sides of the housing, the processor may be used to identify which electrodes provide the most useful stimulation of the desired tissue. This process may be performed using an external programming unit, as described below, that is in communication with the processor 204.

Any processor can be used and can be as simple as an electronic device that produces pulses at a regular interval or the processor can be capable of receiving and interpreting instructions from an external programming unit 208 that allow modification of pulse characteristics. In the illustrated embodiment, the processor 204 is coupled to a receiver 202 which, in turn, is coupled to the optional antenna 224. This allows the processor to receive instructions from an external source to direct the pulse characteristics and the selection of electrodes, if desired.

In one embodiment, the antenna 224 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the stimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 224 and receiver 202 can be used to modify or otherwise direct the operation of the stimulator. For example, the signals may be used to modify the pulses of the stimulator such as modifying one or more of pulse duration, pulse frequency, pulse waveform, and pulse strength. The signals may also direct the stimulator to cease operation or to start operation or to start charging the battery. In other embodiments, the electronic subassembly 212 does not include an antenna 224 or receiver 202 and the processor operates as programmed.

Optionally, the stimulator may include a transmitter (not shown) coupled to the processor and antenna for transmitting signals back to the telemetry unit 206 or another unit capable of receiving the signals. For example, the stimulator may transmit signals indicating whether the stimulator is operating properly or not or indicating when the battery needs to be charged. The processor may also be capable of transmitting information about the pulse characteristics so that a user or clinician can determine or verify the characteristics.

The optional antenna 224 can have any form. In one embodiment, the antenna comprises a coiled wire that is wrapped at least partially around the electronic subassembly within or on the housing.

Any method of manufacture of the components of the system for stimulation can be used. For example, the power source and antenna can be manufactured as described in U.S. Pat. No. 7,437,193. These components can then be placed inside the housing (or, alternatively, the housing can be formed, e.g., molded, around the components).

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead comprising:
    a lead body having a distal end;
    a plurality of electrodes disposed at the distal end of the lead body, wherein each of the plurality of electrodes comprises a unitary ring and a seat in the unitary ring, wherein the unitary ring has a circumference, an exterior surface, and an interior surface, wherein the seat is a first region of the unitary ring that is radially depressed with respect to a second region of the unitary ring adjacent the first region, wherein the seat extends around a portion of the circumference of the unitary ring that is less than an entire extent of the circumference with the second region of the unitary ring extending in both clockwise and counter-clockwise directions around a remaining portion of the circumference of the unitary ring relative to the seat, the seat comprising an exterior surface that is contiguous with the exterior surface of the unitary ring; and
    a plurality of lead wires, each extending along the lead body and attached directly onto, and in contact with, the exterior surface of the seat of a corresponding one of the plurality of electrodes producing an electrical coupling between the lead wire and the corresponding one of the plurality of electrodes.

2. The lead of claim 1, wherein at least one of the plurality of electrodes further comprises an opening spaced apart from edges of the unitary ring and extending from the exterior surface to the interior surface of the unitary ring, wherein the opening intersects the seat.

3. The lead of claim 2, wherein at least one lead wire extends through the opening of at least one of the plurality of electrodes.

4. The lead of claim 1, wherein a terminal end of at least one lead wire is disposed in the seat of at least one of the plurality of electrodes.

5. The lead of claim 1, wherein the plurality of electrodes are disposed in a spaced apart arrangement along the distal end of the lead body.

6. The lead of claim 1, further comprising a plurality of spacers, wherein the electrodes are separated by the spacers.

7. The lead of claim 1, further comprising a lumen tube disposed extending through the plurality of electrodes, wherein the lumen tube comprises at least one lumen.

8. The lead of claim 7, wherein the at least one of the plurality of electrodes further comprises an opening spaced apart from edges of the unitary ring and extending from the exterior surface to the interior surface of the unitary ring and wherein at least one of the lead wires is disposed in the lumen of the lumen tube and extends through the opening of the at least one of the plurality of electrodes.

9. A system for stimulation comprising the lead of claim 1 and a control module, wherein at least one of the lead wires couples the control module to at least one of the plurality of electrodes.

10. A method of making a lead for stimulation, the method comprising:
    providing an electrode comprising a unitary ring having a circumference, an exterior surface, an interior surface, and a seat, wherein the seat is a first region of the unitary ring that is radially depressed with respect to a second region of the unitary ring adjacent the first region, wherein the seat extends around a portion of the circumference of the unitary ring that is less than an entire extent of the circumference with the second region of the unitary ring extending in both clockwise and counter-clockwise directions around a remaining portion of the circumference of the unitary ring relative to the seat, the seat comprising an exterior surface that is contiguous with the exterior surface of the unitary ring;

disposing a terminal end of a lead wire within the seat of the electrode;

electrically coupling the terminal end of the lead wire by attachment of the terminal end directly onto, and in contact with, the exterior surface of the seat of the electrode; and disposing the electrode along a distal portion of a lead with the lead wire extending within the lead.

11. The method of claim 10, further comprising forming an opening on the electrode, wherein the opening is spaced apart from edges of the unitary ring and intersects the seat.

12. The method of claim 11, further comprising disposing the lead wire through the opening of the electrode.

13. The method of claim 10, further comprising stamping the unitary ring to form the seat on the electrode.

14. The method of claim 10, wherein coupling the terminal end of the lead wire comprises welding the terminal end of the lead wire to the seat of the electrode.

15. A lead comprising:

a lead body having a distal end;

a plurality of electrodes disposed at the distal end of the lead body, wherein each of the plurality of electrodes comprises a unitary ring and a seat in the unitary ring, wherein the unitary ring has a circumference, an exterior surface, and an interior surface, wherein the seat is a first region of the unitary ring having a smaller outer diameter than a second region of the unitary ring adjacent to the first region, wherein the seat extends around a portion of the circumference of the unitary ring that is less than an entire extent of the circumference with the second region of the unitary ring extending in both clockwise and counter-clockwise directions around a remaining portion of the circumference of the unitary ring relative to the seat, the seat comprising an exterior surface that is contiguous with the exterior surface of the unitary ring; and a plurality of lead wires, each extending along the lead body and attached directly onto, and in contact with, the exterior surface of the seat of a corresponding one of the plurality of electrodes producing an electrical coupling between the lead wire and the corresponding one of the plurality of electrodes.

16. The lead of claim 15, wherein at least one of the plurality of electrodes further comprises an opening spaced apart from edges of the unitary ring and extending from the exterior surface to the interior surface of the unitary ring, wherein the opening intersects the seat.

17. The lead of claim 16, wherein at least one lead wire extends through the opening of at least one of the plurality of electrodes.

18. The lead of claim 15, wherein a terminal end of at least one lead wire is disposed in the seat of at least one of the plurality of electrodes.

19. The lead of claim 15, wherein the plurality of electrodes are disposed in a spaced apart arrangement along the distal end of the lead body.

20. A system for stimulation comprising the lead of claim 15 and a control module, wherein at least one of the lead wires couples the control module to at least one of the plurality of electrodes.

* * * * *